United States Patent [19]

Miles et al.

[11] 4,436,590

[45] Mar. 13, 1984

[54] DETECTION OF NITRATE ESTERS USING SILVER ELECTRODE

[75] Inventors: Melvin H. Miles; Dwight A. Fine, both of Ridgecrest, Calif.

[73] Assignee: The United States of America as represented by the Secretary of the Navy, Washington, D.C.

[21] Appl. No.: 432,485

[22] Filed: Oct. 4, 1982

[51] Int. Cl.$^3$ ............................................. G01N 27/48
[52] U.S. Cl. ................................................... 204/1 T
[58] Field of Search ..................... 204/1 N, 1 K, 1 T; 436/106, 107

[56] References Cited

U.S. PATENT DOCUMENTS 3,922,205 11/1975 McLean et al. ................... 204/1 T

OTHER PUBLICATIONS

D. A. Shaw et al., ISA Transactions, vol. 15, No. 3, pp. 227–232, (1976).
I. M. Kolthoff et al., "Polarography", vol. I, pp. 359–360, (1952).
M. H. Miles and D. A. Fine, J. Electroanal. Chem., vol. 127, 143–155 (1981).

Primary Examiner—G. L. Kaplan
Attorney, Agent, or Firm—R. F. Beers; W. Thom Skeer; Bruce H. Cottrell

[57] ABSTRACT

A method for the detection of nitrate esters using a solid working electrode of silver, copper, or gold. The method involves the forming of a test solution of a sample and supporting electrolyte, the insertion of the solution into a cell having the solid working electrode, deoxygenation of the test solution, application of a linearly varying potential to the cell and the recording of a voltammogram to show the reduction wave of the nitrate esters.

6 Claims, 2 Drawing Figures

DETECTION OF NITRATE ESTERS USING SILVER ELECTRODE

BACKGROUND OF THE INVENTION

1. Field of the Invention

This invention relates to a method of detecting nitrate esters. In particular, this invention relates to a method of detecting nitrate esters using solid working electrodes.

2. Description of the Prior Art

Nitrate esters are an important class of explosives. Some of these compounds are highly toxic substances with powerful physiological activities. Detection of propylene glycol 1,2-dinitrate (PGDN) and nitroglycerin (NG) in effluent water at military installations has been of considerable importance.

Previous reports on the electrochemical reduction of nitrate esters have been obtained using mercury electrodes. Polarographic methods have proven the most useful detection system for nitrate esters. However, for portable pollution monitoring systems, the dropping mercury electrode is cumbersome to use in the field and poses a toxicity problem in the handling and disposal of the mercury. A method and apparatus for the detection of nitrate esters without the use of the dropping mercury electrode is of considerable interest.

SUMMARY OF THE INVENTION

Accordingly, this invention provides a method for detecting nitrate esters using solid electrodes. The solid electrodes are comprised of a metal selected from the group consisting of silver, gold, and copper. The method comprises the steps of forming a test solution, placing the solution into a cell with a solid working electrode, deoxygenating the solution, applying a linearly varying potential over the range of $-0.3$ V to $-1.0$ V (vs. SCE) to the cell, and recording a voltammogram as the potential is applied.

OBJECTS OF THE INVENTION

It is an object of this invention to provide a voltammetric method of detecting nitrate esters.

Another object of the invention is to provide a method of detecting nitrate esters without the use of the dropping mercury electrode.

Still another object of the invention is to provide a method of detecting nitrate esters with solid working electrodes.

These and other objects of the invention will become apparent from the following specification when taken with the drawings.

DESCRIPTION OF THE PREFERRED EMBODIMENT

The present invention provides a method of detecting nitrate esters in solution with a solid working electrode. The electrochemical reduction of the nitrate esters, propyleneglycol 1,2-dinitrate (PGDN) and nitroglycerin (NG) is dependent on the choice of electrode materials. It is found that the reduction of PGDN is readily observed on only silver, copper, gold and mercury electrodes. Metals that are generally among the best electrocatalysts such as platinum, and iridium, are completely inactive as are nickel, tungsten and molybdenum electrodes.

Figure 1:
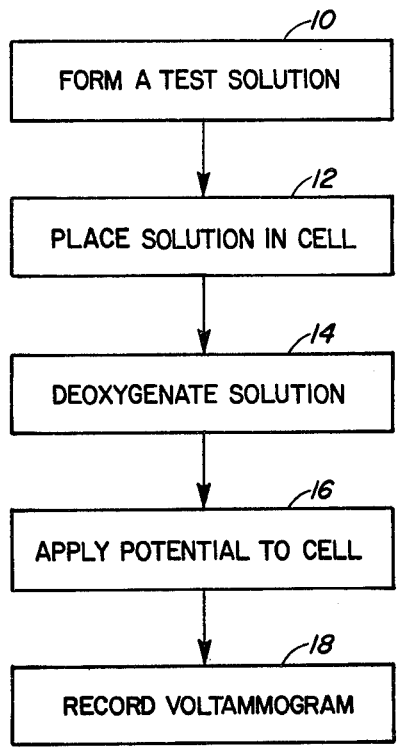
FIG. 1 is a flow diagram of the detection method.

Referring to FIG. 1, the initial step of this method is to form a test solution as shown at box 10. A sample solution to be tested is mixed with a supporting electrolyte solution. The supporting electrolyte carries the electrical current, hence mass transport of the test substance is essentially by diffusion. A suitable supporting electrolyte solution is a 0.10 M $NaHCO_3$/0.1 M $Na_2CO_3$ buffer (pH=10.3). A solution of 0.01 M NaOH with 0.5 M NaCl can also serve as the supporting electrolyte.

Next the test solution is placed into an electrochemical cell as shown at box 12. Electrochemical measurements can be made in the cell having a cylindrical container equipped with a cap that supports the solid working electrode, a platinum wire spiral counter electrode, a reference electrode, and an inert gas stirring tube. A saturated calomel electrode can serve as the reference electrode. The SCE reference electrode (Beckman Co.) has a ceramic junction that gives a negligible leak rate. The cylindrical container can be constructed of glass.

The test solution is then deoxygenated as shown at box 14. The bubbling of an inert gas such as nitrogen or helium through the electrolyte with simultaneous strong agitation by stirring with a magnetic stir bar can be used to remove the oxygen from the solution. The oxygen must be removed to prevent an oxygen reduction wave from interfering with the nitrate ester under study.

Box 16 shows that a linearly varying potential is next applied to the cell. The potential is applied over the range of $-0.3$ V to $-1.0$ V (vs. SCE). The electrochemical measurements can be obtained with the use of a P.A.R. Model 174 polarographic analyzer. The linearly varying potential is applied at a potential sweep rate of between 5 to 100 mV/s.

As the potential is applied, a voltammogram is recorded as shown at Box 18. The voltammogram may be recorded with any suitable recorder such as an X-Y recorder (Hewlett-Packard 7047A).

The use of the solid silver electrode as the working electrode is believed to be the best mode of practicing this invention. A suitable silver wire electrode used was 0.080 cm in diameter and 1.5 cm in length, to give a geometric area of 0.38 $cm^2$. The silver wire was spot welded to a nickel lead and sealed in glass tubing with epoxy. Although silver electrodes were usually cleaned mechanically with wet carborundum paper (600A) prior to use, no adverse affects were detected when this cleaning was omitted. Electrochemical conditioning of the electrode by several potential scans at 100 mV/s over the range of interest were important to good results.

For the accurate detection of small amounts of nitrate esters by the measurement of current densities in the small $\mu A/cm^2$ region, the design of the electrode was found to be an important factor. The area of possible cracks or crevices about the electrode seal must be kept as small as possible relatively to the effective electrode area. For example wire electrodes performed much better than small disc or spherical electrodes with their relatively large areas of contact with glass or epoxy seals.

Figure 2:
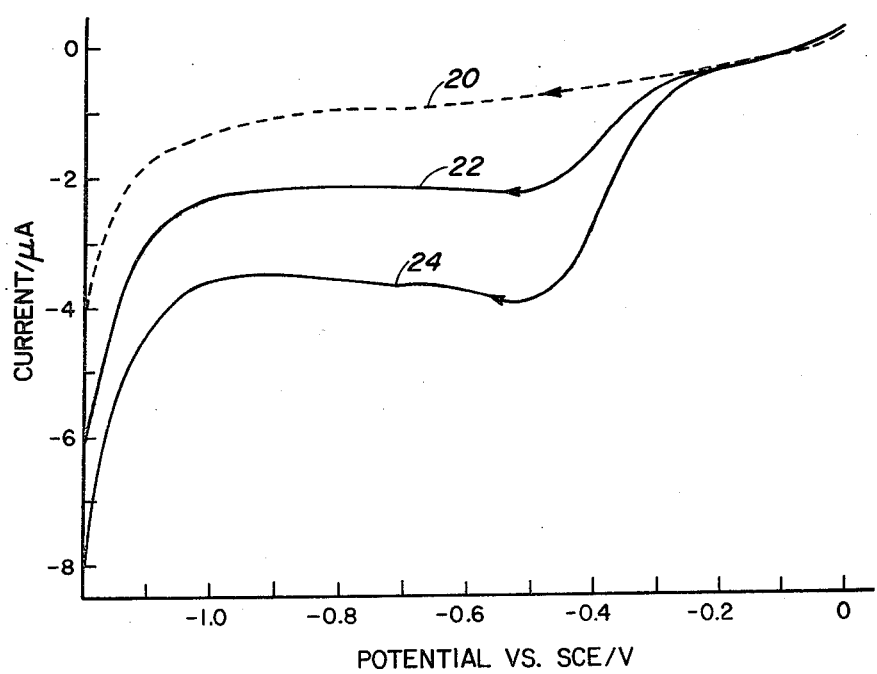
FIG. 2 is a voltammetric trace using a silver wire electrode.

Referring to FIG. 2 a linear sweep voltammetric trace on a silver wire electrode is shown. The potential sweep rate was 5 mV/s. Line 20 shows the background current with no nitrate ester present. Line 22 shows the trace with 3.8 ppm of PGDN. A trace for a sweep with 8.0 ppm of PGDN is shown at 24.

EXAMPLE

An aqueous stock solution containing 85 ppm PGDN was prepared by weighing out 1.78 g of a mixture of 10 g PGDN dissolved in 200 g of acetone. This is then diluted to 1.0 l. Solutions in the 0–10 ppm range were obtained by pipetting a calculated amount of the 85 ppm solution into 50 ml of the electrolyte solution. All experiments were conducted at room temperature (22°–23° C.).

Slower potential sweep rates give a more sensitive detection of nitrate esters as interfering background current decreases faster with decreasing potential scan rate than the diffusion controlled peak current. The background current is due mainly to double layer charging or to adsorption pseudo capacity effects. An increase in sensitivity for nitrate ester detection can be obtained by the rapid stirring of the solution. The presence of PGDN at concentrations as low as 0.1 ppm can be detected at 5 mV/s in rapidly stirred solutions. Measurements of the current at a constant potential in stirred solutions also indicate a detection limit of about 0.1 ppm on silver electrodes.

The peak current in the reduction waves of the nitrate esters was found at potentials between $-0.5$ to $-0.8$ V (vs. SCE) as shown at 22 and 24. The potential can vary depending on the electrolyte in the solution. The PGDN reduction wave is shifted to more negative potentials with increasing polarizability of the anion. Specific anion adsorption increases in the order $F \leq Cl < Br < I$ on silver, as it does for other metals.

Obviously, many modifications and variations of the present invention are possible in light of the above teachings. It is therefore to be understood that, within the scope of the appended claims, the invention may be practiced otherwise than as specifically described.

What is claimed is:

1. A method of detecting nitrate esters in a sample solution using a voltammetric instrument with a solid working electrode comprising the steps of:
   forming a test solution by mixing a sample solution with a supporting electrolyte solution;
   placing said test solution into a cell having a solid working electrode selected from the group consisting of silver, gold and copper, a counter electrode and a reference electrode;
   deoxygenating said test solution;
   applying a linearly varying potential over the range of $-0.3$ V to $-1.0$ V (vs. SCE) to said cell; and
   recording a voltammagram with a recorder as the potential is applied whereby said nitrate esters are detected as a wave in a voltammetric scan.

2. A method of detecting nitrate esters as in claim 1 wherein said solid working electrode is a solid silver electrode.

3. A method of detecting nitrate esters as in claim 1 wherein said solid working electrode is a solid gold electrode.

4. A method of detecting nitrate esters as in claim 1 wherein said applying potential step occurs at a rate of 5 mV/s.

5. A method of detecting nitrate esters as in claim 1 wherein said applying potential step occurs at a rate of 100 mV/s.

6. A method of detecting nitrate esters as in claim 1 wherein said applying potential step occurs at a rate of from 5–100 mV/s.

* * * * *